US005952514A

United States Patent [19]

Darsow

[11] Patent Number: 5,952,514

[45] **Date of Patent: *Sep. 14, 1999**

[54] PROCESS FOR PREPARING SUCCINIC ANHYDRIDE

[75] Inventor: Gerhard Darsow, Krefeld, Germany

[73] Assignee: Bayer Aktiengesellschaft, Leverkusen, Germany

[ * ] Notice: This patent is subject to a terminal disclaimer.

[21] Appl. No.: 09/006,768

[22] Filed: Jan. 14, 1998

[30] Foreign Application Priority Data

Jan. 22, 1997 [DE] Germany .......................... 197 02 039

[51] Int. Cl.[6] .................................... C07D 307/60

[52] U.S. Cl. .................................... 549/233

[58] Field of Search .................................... 549/233

[56] References Cited

U.S. PATENT DOCUMENTS

| | | | |
|---|---|---|---|
| 2,198,153 | 4/1940 | Coons et al. | 260/341 |
| 5,770,744 | 6/1998 | Darsow | 549/233 |

FOREIGN PATENT DOCUMENTS

| | | | |
|---|---|---|---|
| 0722924 | 7/1996 | European Pat. Off. | C07C 51/567 |
| 1226556 | 10/1966 | Germany . | |
| 48-7609 | 3/1973 | Japan . | |
| 507592 | 8/1939 | United Kingdom . | |

OTHER PUBLICATIONS

Patent Abstracts of Japan, Abstract of JP 08 245 611 (Sep. 24, 1996).

Gregg, et al., Adsorption, Surface Area and Porosity, London 1982, Chapter 2, p. 41, Chapter 6, p. 283.

F.M. Nelsen, et al., Determination of Surface Area: Adsorption Measurements by a Continuous flow Method, vol. 30, No. 8, (1958) pp. 1337–1390.

Chemical Abstracts, vol. 34, p. 5466 (1940) Kenneth W. Coons, Hydrogenation of Maleic Anhydride, abstract of referenced U.S. 2,198,153.

Chemical Abstracts 71047b, vol. 93, p. 912 (1980) A. Avots, et al., Succinic Anhydride, abstract of U.S.S.R. 721, 406.

English–language abstract of EP–722924 (Jul. 24, 1996).

*Primary Examiner*—Bernard Dentz

*Attorney, Agent, or Firm*—Joseph C. Gil; Diderico van Eyl

[57] ABSTRACT

Maleic anhydride can be hydrogenated to succinic anhydride with particularly high conversion rates by a catalytic liquid-phase hydrogenation with hydrogen, by carrying out the hydrogenation continuously at a pressure of 10 to 400 bar and a reaction temperature of 60 to 180° C. on oxygen-free and support-free shaped bodies, which are arranged in the fixed bed, of compressed powders of the elements of the iron sub-group of group VIII of the Periodic Table, mixed or alloyed with elements of transition group IV and/or V; in addition, hydrogenation-inert elements can be present. The shaped bodies have a compressive strength of 20 to 220 N and an internal surface area of 10 to 100 $m^2/g$.

16 Claims, No Drawings

PROCESS FOR PREPARING SUCCINIC ANHYDRIDE

BACKGROUND OF THE INVENTION

1. Field of the Invention

The present invention relates to an inexpensive process which proceeds continuously with particularly high conversion rates for preparing succinic anhydride in which only extremely small amounts of the γ-butyrolactone usually formed as byproduct in the hydrogenation of maleic anhydride and no mono- or hydroxycarboxylic acids having carbon numbers <4 are formed.

Succinic anhydride is an important starting material for preparing thermoplastic polyesters, which have particular mechanical and chemical properties and good biodegradability.

2. Description of the Related Art

It is known to prepare succinic anhydride from succinic acid batchwise by a dehydration reaction by introducing acetic anhydride vapors into molten succinic acid (GB 507 592). It is further known to hydrogenate maleic anhydride to give succinic anhydride in a batch process over Ni (U.S. Pat. No. 2,198,153, cited in Chem. Abstracts 34 (1940), $5465^9$) or Pd, Rh, $Pt/Al_2O_3$ (JP 48-7609 (1973)). It is further known to hydrogenate maleic anhydride to succinic anhydride continuously over Pd/activated carbon (SU 721 406; cited in Chem. Abstracts 93(1980), 71047 b). In addition, it is known to hydrogenate maleic anhydride to succinic anhydride over catalysts of Cu molybdate, tungstate, chromate and/or vanadate, Co molybdate, tungstate, chromate and/or vanadate and/or Ni molybdate, tungstate, chromate and/or vanadate, for which the supports used are shaped silica strands (DE 1 226 556).

The course of the reaction is shown by the following reaction scheme:

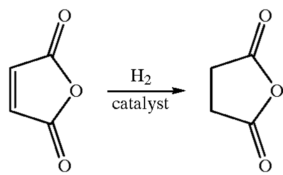

In the known processes for preparing succinic anhydride, batchwise suspension processes are predominantly used in which the maleic anhydride is hydrogenated with hydrogen with and without solvent over pulverulent catalysts. Batch processes have the disadvantage that their capacity is very small relative to the reaction volume, and large reaction apparatuses and storage tanks are thus required. Energy consumption and labor requirements are relatively high.

Continuous powder catalyst processes which operate with a plurality of hydrogenation reactors connected in cascade avoid some of these disadvantages. However, there is still the requirement for repeatedly specifically metering the pulverulent catalysts, circulating them by pumping and quantitatively filtering them off from the reaction product. The catalyst slurry pumps are subject to high mechanical wear. The quantitative removal of the pulverulent catalysts from the reaction product is costly. In addition, there is a high risk of relatively rapidly decreasing the catalyst activity by the additional operations. It is advantageous, therefore, to make the reaction proceed over fixed-bed catalysts. Catalysts of this type need to have a high activity which must not decrease over a prolonged period, since frequent catalyst changes in fixed-bed reactions are likewise costly. A continuous process which has been previously described is the hydrogenation of maleic anhydride to succinic anhydride over Pd/activated carbon or Cu molybdate, tungstate, chromate and/or vanadate, Co molybdate, tungstate, chromate and/or vanadate and/or Ni molybdate, tungstate, chromate and/or vanadate on silica supports (DE 1 226 556). These catalysts had only a restricted life. In addition, the reaction can generally only be carried out using a solvent.

In addition, it has been found that maleic anhydride can be hydrogenated to succinic anhydride over support-free shaped bodies which are arranged in the fixed bed and comprise oxygen-free metal powders of one or more elements of the iron subgroup of group VIII of the Periodic Table of the Elements (Mendeleev), for which it can be useful to alloy the metals of the iron subgroup with activating elements of transition group VI of the Periodic Table. In this process the powders used for preparing the shaped bodies can additionally include small proportions of non-catalytic elements (eg. silicon, aluminum, titanium, carbon) (EP 722 924 A). However, the conversion rates at space velocities of 0.14–0.4 kg of maleic anhydride per 1 of catalyst·h are very low.

SUMMARY OF THE INVENTION

Surprisingly, it has now been found that maleic anhydride can very readily be continuously hydrogenated to succinic anhydride at considerably higher conversion rates (eg. 0.6–1.4 kg of maleic anhydride per 1 of catalyst·h) on support-free shaped bodies which are arranged in a fixed bed and comprise oxygen-free metal powders of one or more elements of the iron subgroup of group VIII of the Periodic Table of the Elements (Mendeleev) which are additionally alloyed with one or more activating elements of transition group IV and/or V of the Periodic Table. In this process, the powders used can additionally contain certain proportions of non-catalytic elements (eg. silicon, aluminum, carbon) without the high activity being decreased. The solid bodies must have a compressive strength of 20–220 N and an internal surface area of 10–100 $m^2/g$.

The invention thus relates to a process for the continuous preparation of succinic anhydride by catalytic hydrogenation of maleic anhydride, which comprises carrying out the hydrogenation in the liquid phase at an $H_2$ pressure of 10–400 bar, with a 10–80 fold molar amount of $H_2$, based on the stoichiometric amount, and at a temperature of 60–180° C. on oxygen-free and support-free catalysts which are arranged in a fixed bed, the catalysts being present as compressed shaped bodies produced from metal powders, which shaped bodies have a compressive strength of 20–220 N and an internal surface area of 10–100 $m^2/g$ and in which the metal powders include at least 50% by weight of one or more elements of the iron group of group VIII of the Periodic Table of the Elements (Mendeleev), mixed or alloyed with at least 6% by weight of one or more metals of transition group IV and/or V of the Periodic Table and include 0 to 20% by weight of one or more hydrogenation-inert elements from the group consisting of aluminum, silicon and carbon, all figures based on the total weight of the metal powder.

DETAILED DESCRIPTION OF THE INVENTION

The compressive strength of the support-free shaped bodies can be determined as specified by DIN 50106.

Support-free shaped bodies can be tested for the claimed internal surface areas and thus for usability in the process according to the invention by methods which are described by F. M. Nelsen and F. T. Eggertsen, Analyt. Chem. 30 (1958), pp. 1387–1390 and S. J. Gregg and K. S. W. Sing, Adsorption, Surface Area and Porosity, London 1982, Chapters 2 and 6.

The iron subgroup of transition group VIII of the Periodic Table of the Elements (Mendeleev) includes the elements iron, cobalt and nickel. The support-free shaped bodies to be used according to the invention include one or more of these metals in amounts of at least 50, preferably at least 60, in particular at least 65%, by weight, based on the total weight of the support-free shaped bodies.

Transition group IV of the Periodic Table includes the elements titanium, zirconium and hafnium. Transition group V of the Periodic Table includes the elements vanadium, niobium and tantalum. The support-free shaped bodies to be used according to the invention include one or more of these metals in amounts of at least 6.0% by weight, preferably at least 9.5% by weight, based on support-free shaped bodies; they include one or more of these metals in amounts of at most 30, preferably at most 15%, by weight, based on support-free shaped bodies. Preferably, said elements include zirconium, hafnium, vanadium, niobium and tantalum, particularly preferably zirconium and vanadium.

The support-free shaped bodies to be used according to the invention can, in addition, include up to 20, preferably up to 15%, by weight of other elements, in each case based on support-free shaped bodies; examples of such elements, which are not catalytically active, include aluminum, silicon and carbon. According to a preferred embodiment, the support-free shaped bodies include, in addition to the metals of group VIII and transition group IV and/or V, no more than 15% by weight of aluminum and no more than 5% by weight of other elements.

For the hydrogenation process, a pure hydrogen is used which has been precompressed to a pressure of 10–400 bar, preferably 30 to 400 bar, particularly preferably 50–300 bar, employing 10–80-fold, preferably 20- to 40-fold, molar amounts of hydrogen, based on the stoichiometric amount.

The hydrogenation is performed continuously in the fixed-bed process on the support-free shaped bodies of the type described which serve as hydrogenation catalysts, by passing the liquid maleic anhydride to be hydrogenated either ascending from bottom to top, co-currently with the previously admixed hydrogen, over the shaped bodes packed into the hydrogenation reactor, or passing it, entering from the bottom, in the opposite direction to the hydrogen flowing in from the top (counter-current process). The process according to the invention can obviously also be carried out in solvents. Suitable solvents which may be used conjointly and are inert under the reaction conditions are, for example, di-n-propyl ether, di-iso-propyl ether, di-n-butyl ether, di-iso-butyl ether, tetrahydrofuran, dioxane, γ-butyrolactone. Preferably, the process according to the invention is carried out without solvent or in γ-butyrolactone as solvent inherent to the system.

The hydrogenation process is carried out at temperatures from 60 to 180° C., preferably 80–160° C., particularly preferably 100–140° C. Lower temperatures require longer residence times or the abandonment of quantitative conversion. Higher temperatures lead to increased formation of γ-butyrolactone as byproduct.

The space velocity is 600 to 1400 g of maleic anhydridesl of catalyst per hour.

Maleic anhydride is generally used in the industrially available quality grade, preferably having a purity >99%. However, distillation refluxes, eg. of γ-butyrolactone, having maleic anhydride present therein, may also be used.

The hydrogenation reactor can either a single high-pressure tube made of steel or a steel alloy which is wholly or partially filled with the support-free shaped bodies, in which case the use of holders (wire baskets and the like) can also be beneficial, or else a jacketed high-pressure tube bundle whose individual tubes are wholly or partially filled with shaped bodies.

The support-free shaped bodies can be produced by conventional methods by compressing the metal powders under high pressure in tableting or pelleting machines, possibly also using graphite in amounts of 0.5–1.5% by weight, based on the total weight of the constituents forming the catalyst, or adhesives in small amounts, to improve the adherence of the metal particles. The support-free shaped bodies are preferably produced in an oxygen-free atmosphere in order to avoid surface oxidations. The most effective shaped bodies and those most expedient for the reaction procedure are tableted or pelleted shapes bodies having diameters of 2–10 mm, preferably of 3 to 7 mm. The compressive strength of the shaped bodies, which according to the invention is 20 to 220 N, preferably 60 to 200 N, is of considerable importance. Lower compressive strengths lead to disintegration of the shaped body or erosive wear, which would cause metallic contamination of the reaction product. Higher values necessitate a disproportionate expenditure on the compressing, without further advantages being achieved. The internal surface area of the shaped bodies, which according to the invention is 10 to 100 $m^2/g$ and is decisive for substantially quantitative conversion of the starting materials, is also of considerable importance. Under the reaction conditions described, it is possible in this manner, highly unexpectedly, to achieve long catalyst service lives of 15,000 hours and more, which leads to catalyst consumptions of <0.1% by weight, based on the reaction product prepared. The oxygen-free and support-free fixed-bed catalysts to be used according to the invention do not, in contrast to supported catalysts, have a tendency to "bleed", ie. do not have a tendency for there to be transfer of catalyst constituents in ionic or colloidal form into the solution phase of the substrate, so that the substrate is not contaminated by heavy metals, which can usually be removed from the substrate only with difficulty, for example using ion exchangers. The catalyst metals to be used can be readily reprocessed, for example after prolonged use of the catalyst, and reused, since the heavy metals do not need to be laboriously separated from a support material.

The reaction mixture leaving the hydrogenation reactor is decompressed, and the excess hydrogen can be collected and, after compression and replenishment of consumed hydrogen, reused. In the case of a complete hydrogenation (99.9 to 100% conversion of the maleic anhydride), the reaction mixture consists of at least 98% by weight succinic anhydride. It can include up to 1.6% by weight of organic low-boilers, principally as γ-butyrolactone. The succinic anhydride produced has a content of catalyst constituents of <1 ppm, is obtained in a purity of ≧99.9% by weight after removal of the low-boilers by distillation and is therefore suitable without any further purification for farther use, for example also for preparing polymers. The colorless and glass-clear melt of succinic anhydride obtained after the distillation can either be crystallized in crystallization apparatuses of conventional type or be processed on flaking rollers to give free-flowing flakes.

EXAMPLES

Example 1

A vertical thermally insulated high-pressure tube made of stainless steel of internal diameter 45 mm and length 1 m was filled with 1.2 1 of a catalyst which was produced by tableting a metal powder of an Ni/Zr/Al alloy having a Zr content of 14.9% by weight and an Al content of 10.5% by weight and which, at a cylinder height of 5 mm and a diameter of 5 mm, had a compressive strength of 78 N on the curved cylindrical surface and an internal surface area of 81 $m^2/g$. 700 g of a glass-clear melt of maleic anhydride prepared in a melt kettle together with 20 times the molar amount of high-purity hydrogen, at a pressure of 300 bar, were continuously pumped per hour through this tube, ascending from bottom to top. Maleic anhydride melt and hydrogen had previously been passed together through a heat exchanger and heated so that they entered the high-pressure tube at a temperature of 125° C. The mixture of liquid reaction product and excess hydrogen leaving the high-pressure tube was passed to a separator, from where the hydrogen, after replacement of the amount consumed, was, together with new maleic anhydride melt, pumped back to the preheater and from there again into the high-pressure tube.

The colorless and clear melt of the reaction product was, after decompression to atmospheric pressure and cooling, analyzed by gas chromatography. It no longer contained maleic anhydride and, of organic low-boilers, only contained 1.2% by weight of γ-butyrolactone, so that the succinic anhydride content of the reaction product was 98.8% by weight. The succinic anhydride produced was obtained in a purity of 99.9% by weight after removal of the low-boilers by distillation.

The catalyst was unchanged in activity after a running time of 3600 hours, so that the composition of the reaction product did not change over this period.

Example 2

In a high-pressure tube as in Example 1, at a temperature of 125° C. and a hydrogen pressure of 200 bar, the hydrogen was passed in the opposite direction to the ascending maleic anhydride melt, in the opposite direction of reaction flow as in Example 1, the same amount being hydrogenated per hour as in Example 1. The catalyst had been produced by tableting a pulverized Ni/Fe/Zr alloy. The alloy had an Fe content in the nickel of 5.4% by weight and a Zr content of 10.9% by weight. The tablets, at a cylinder height of 5 mm and a diameter of 5 mm, had a compressive strength of 107 N on the curved cylindrical surface and an internal surface area of 93 $m^2/g$. After a running time of 1200 hours, the conversion of the maleic anhydride used was 99.9% by weight. The content of γ-butyrolactone in the reaction product was 1.6% by weight, so that the succinic anhydride content of the reaction product was 98.3% by weight (remainder=0.1% by weight of unreacted maleic anhydride). After removal of the impurities by distillation, the succinic anhydride produced was obtained in a purity of 99.9% by weight.

Example 3

A vertical thermally insulated high-pressure tube made of stainless steel of internal diameter 45 mm and length 1 m was filled with 1.21 of a hydrogenation catalyst which was produced by tableting powder of a Ni/Zr/V/Al alloy and which, at a cylinder height of 5 mm and a diameter of 5 mm, had a compressive strength of 106 N on the curved cylindrical surface and an internal surface area of 81 $m^2/g$. The alloy had a Zr content of 14.9% by weight, a V content of 12.1% by weight and an Al content of 10.2% by weight. 800 g of maleic anhydride melt, together with thirty times the molar amount of high-purity hydrogen, at a pressure of 300 bar, were pumped per hour through the high-pressure tube ascending from bottom to top. Maleic anhydride melt and hydrogen were brought to a temperature of 120° C. before entry into the high-pressure tube. After a running time of 1280 hours, the conversion of the maleic anhydride used was 100% by weight. The content of γ-butyrolactone in the reaction product was 1.0% by weight, so that the succinic anhydride content was 99.0% by weight. After removal of the impurity by distillation, the succinic anhydride produced was obtained in a purity of 99.9% by weight.

Example 4

In a high-pressure tube as in Example 1, but made of N9 high-pressure steel, the same amount of maleic anhydride per hour was hydrogenated at a temperature of 120° C. and a hydrogen pressure of 300 bar. The catalyst had been produced by tableting powder of an Ni/V/Al alloy having a V content of 12.1% by weight and an Al content of 6.1% by weight. The tablets, at a cylinder height of 5 mm and a diameter of 5 mm, had a compressive strength of 97 N and an internal surface area of 85 $m^2/g$. After a running time of 800 hours, the content of succinic anhydride in the reaction product was 99.1% by weight and the content of γ-butyrolactone was 0.9% by weight.

Example 5

In a high-pressure tube as in Example 1, an amount of 700 g of maleic anhydride was hydrogenated per hour at a temperature of 130° C. and a hydrogen pressure of 300 bar. The catalyst had been produced by tableting a pulverized Ni/Zr alloy having a Zr content of 9.2% by weight. The tablets, at a cylinder height of 5 mm and a diameter of 5 mm, had a compressive strength of 118 N and an internal surface area of 98 $m^2/g$. After a running time of 400 hours, the conversion of the maleic anhydride used was 99.9% by weight. The content of γ-butyrolactone in the reaction product was 1.0% by weight, so that the succinic anhydride content was 98.9% by weight (remainder=0.1% by weight of unreacted maleic anhydride).

Example 6

In a high-pressure tube as in Example 1, 800 g of maleic anhydride, dissolved as a 30% strength by weight solution in γ-butyrolactone, were hydrogenated per hour at a temperature of 120° C. and a hydrogen pressure of 300 bar. The catalyst had been produced by tableting a pulverized Ni/Zr/Al/Si alloy having a Zr content of 9.8% by weight, an Al content of 6.1% by weight and an Si content of 2.1% by weight. The tablets, at a cylinder height of 5 mm and a diameter of 5 mm, had a compressive strength of 116 N on the curved cylindrical surface and an internal surface area of 88 $m^2/g$. After a running time of 680 hours, the conversion of the maleic anhydride used was 99.9% by weight. After removing the solvent by distillation and a subsequent distillation of the crude succinic anhydride, the latter had a purity of 99.95% by weight. The γ-butyrolactone distilled off was recycled as solvent back to the process.

What is claimed is:

1. A process for the continuous preparation of succinic anhydride by catalytic hydrogenation of maleic anhydride, which comprises carrying out the hydrogenation in the liquid phase at an $H_2$ pressure of from 10 to 400 bar, with a 10–80 fold molar amount of $H_2$, based on the stoichiometric amount, and at a temperature of from 60 to 180° C. on oxygen-free and support-free catalysts which are arranged in a fixed bed, the catalysts being present as compressed shaped bodies produced from metal powders, which shaped bodies have a compressive strength of from 20 to 220 N and an internal surface area of from 10 to 95 $m^2/g$ and in which the metal powders include at least 50% by weight of one or more elements of the iron group of group VIII of the Periodic Table of the Elements (Mendeleev), mixed or alloyed with at least 6% by weight of one or more metals of transition group IV and/or V of the Periodic Table and include 0 to 20% by weight of one or more hydrogenation-inert elements from the group consisting of aluminum, silicon and carbon, all figures based on the total weight of the metal powder.

2. The process of claim 1, wherein the metal powders contain at least 60% by weight of one or more elements of the iron group.

3. The process of claim 2, wherein the metal powders contain at least 65% by weight of one or more elements of the iron group.

4. The process of claim 1, wherein the metal powders have a content of at least 7.5% by weight of elements of transition group IV and/or transition group V.

5. The process of claim 4, wherein the metal powders have a content of at least 9% by weight of elements of transition group IV and/or transition group V.

6. The process of claim 1, wherein the metal powders contain at most 30% by weight of elements of transition group IV and/or V.

7. The process of claim 6, wherein the metal powders contain at most 20% by weight of elements of transition group IV and/or V.

8. The process of claim 7 wherein the metal powders contain at most 15% by weight of elements of transition group IV and/or V.

9. The process of claim 1, wherein the metal powders have, when hydrogenation-inert elements are present, a content of from 0 to 15% by weight of aluminum and from 0 to 5% by weight per element of Si and C.

10. The process of claim 1, wherein the shaped bodies have a compressive strength of from 70 to 140 N.

11. The process of claim 1, wherein the shaped bodies are cylindrical or spherical and have diameters of 2–10 mm.

12. The process of claim 11, wherein the shaped bodies have diameters of 3 to 7 mm.

13. The process of claim 1, wherein the hydrogenation is carried out at a $H_2$ pressure of from 30 to 400 bar.

14. The process of claim 13, wherein the $H_2$ pressure is of 50–300 bar.

15. The process of claim 1, wherein a 20 to 40-fold molar amount of $H_2$ is employed.

16. The process of claim 1, wherein the maleic anhydride passes through the hydrogenation reactor ascending from bottom to top, whereas the hydrogen required for the hydrogenation is either pumped into the reactor together with the maleic anhydride or passed in the opposite direction to this, flowing from top to bottom.

* * * * *